US008552030B2

(12) United States Patent
Prakasam et al.

(10) Patent No.: US 8,552,030 B2
(45) Date of Patent: Oct. 8, 2013

(54) PROCESS FOR THE PREPARATION OF D-THREO-RITALINIC ACID HYDROCHLORIDE BY RESOLUTION OF DL-THREO-RITALINIC ACID USING CHIRAL CARBOXYLIC ACID

(75) Inventors: Tangirala Prakasam, Chennai (IN); Borkatte Narasimha Hitesh Kumar, Chennai (IN); Sangu Perumal, Kanchipuram Dt. (IN); Kothandapani Loganathan, Chennai (IN)

(73) Assignee: Malladi Drugs & Pharmaceuticals Ltd., Chennai (IN)

( * ) Notice: Subject to any disclaimer, the term of this patent is extended or adjusted under 35 U.S.C. 154(b) by 440 days.

(21) Appl. No.: 13/055,472

(22) PCT Filed: Jul. 3, 2009

(86) PCT No.: PCT/IN2009/000378
§ 371 (c)(1),
(2), (4) Date: Jan. 24, 2011

(87) PCT Pub. No.: WO2010/128517
PCT Pub. Date: Nov. 11, 2010

(65) Prior Publication Data
US 2011/0130569 A1    Jun. 2, 2011

(30) Foreign Application Priority Data

May 7, 2009 (IN) .......................... 1062/CHE/2009

(51) Int. Cl.
*A61K 31/445* (2006.01)
(52) U.S. Cl.
USPC ........................................................ 514/317
(58) Field of Classification Search
USPC ........................................................ 514/317
See application file for complete search history.

(56) References Cited

U.S. PATENT DOCUMENTS

| 2,957,880 A | 6/1958 | Rometsch |
| 6,100,401 A | 8/2000 | Prashad et al. |
| 6,121,453 A | 9/2000 | Zavareh |
| 6,162,919 A | 12/2000 | Prashad et al. |
| 6,242,464 B1 | 6/2001 | Harris et al. |
| 6,441,178 B2 | 8/2002 | Zavareh et al. |
| 7,247,730 B2 | 7/2007 | Gutman et al. |

FOREIGN PATENT DOCUMENTS

| WO | WO97/27176 | 7/1997 |
| WO | WO97/32851 | 9/1997 |
| WO | WO98/25902 | 6/1998 |

*Primary Examiner* — John Mabry
(74) *Attorney, Agent, or Firm* — Alan Kamrath; Kamrath IP Lawfirm, P.A.

(57) ABSTRACT

The invention disclosed in this application relates to an improved process for the manufacture of d-threo-ritalinic acid hydrochloride and l-threo-ritalinic acid hydrochloride in an optically pure form by the resolution of dl-threo-ritalinic acid using a chiral carboxylic acid The d-threo-ritalinic acid hydrochloride prepared by the process of the present invention on esterification gives d-threo-methylphenidate, a very well known CNS stimulant.

18 Claims, No Drawings

PROCESS FOR THE PREPARATION OF D-THREO-RITALINIC ACID HYDROCHLORIDE BY RESOLUTION OF DL-THREO-RITALINIC ACID USING CHIRAL CARBOXYLIC ACID

FIELD OF THE INVENTION

The objective of the present invention relates to improved process for the manufacture of a d-threo-ritalinic acid hydrochloride and l-threo-ritalinic acid hydrochloride in an optically pure form by the resolution of dl-threo-ritalinic acid using a chiral carboxylic acid.

BACKGROUND OF INVENTION

Methylphenidate available in the market to treat Attention Deficient Hyperactivity Disorder (ADHD) is dl-threo mixture. It is a controlled substance. Methylphenidate contains two chiral carbon atoms and so exists in four enantiomeric forms. Of all the forms, the studies of its threo-diastereomer revealed that d-threo isomer has been found to be more active and also showed significant metabolic difference than l-threo enantiomer.

To date, there have been several methods disclosed in the literature for preparing d-threo enantiomer of methylphenidate. For example, the process reported first by Patrick et. al. [*The Journal of Pharmacology and Experimental Therapeutics*, 241, 152-158 (1987)], describes the use of expensive resolving agent, 1,1'-binaphthyl-2,2'-diyl hydrogen phosphate in the resolution of dl-threo-methylphenidate. More efficient resolutions, using a O,O-Diaroyltartaric acid or menthoxy-acetic acid or dibenzoyl-D-tartaric acid are disclosed in WO9727176, GB97/00643, U.S. Pat. No. 6,100,401, U.S. Pat. No. 6,121,453, U.S. Pat. No. 6,162,919 and U.S. Pat. No. 6,242,464. Resolution of threo-methylphenidate may also be achieved by enzymatic hydrolysis methods proposed by Prashad (1998) [U.S. Pat. No. 7,247,730] and in WO98/25902.

U.S. Pat. No. 2,957,880 discloses the resolution of erythro-phenylpiperidyl acetamide using tartaric acid. This, however, must be followed by amide hydrolysis and equilibration at the benzylic centre, to give the threo isomer of the ritalinic acid.

In addition, U.S.2002/0019535 describes the manufacture of threo-ritalinic acid by resolution of threo-ritalinic acid hydrochloride using chiral base (S)-(−)-1-phenethylamine affording the product in 77% ee.

It would be desirable to find
1) a satisfactory substrate for resolution that did not involve handling of the active drug and
2) a more practical and efficient process to produce compound with high optical purity. Ritalinic acid in threo form might be a target. threo-Ritalinic acid contains a carboxylic group and a tertiary amino function in the moiety, due to which either chiral carboxylic acid or chiral organic base can be used for resolution. The d-threo-enantiomer of ritalinic acid thus obtained can be converted to d-threo-methylphenidate hydrochloride by reaction with methanol and hydrochloric acid.

The present invention provides an improved process for preparing d- and l-threo isomers of ritalinic acid of formula I & II,

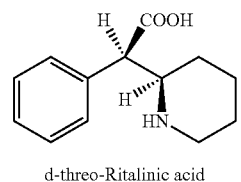

d-threo-Ritalinic acid (Formula I)

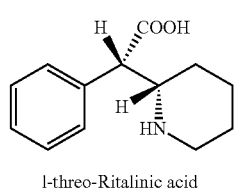

l-threo-Ritalinic acid (Formula II)

and its salt by resolution of dl-threo-ritalinic acid of the formula III using chiral carboxylic acid of the formula IV as the resolving agent.

dl-threo-Ritalinic acid (Formula III)

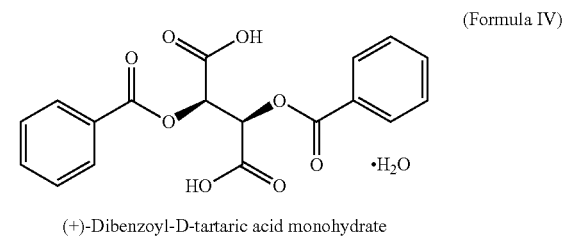

(+)-Dibenzoyl-D-tartaric acid monohydrate (Formula IV)

The method of the present invention is quite preferable and economical for the preparation of d-threo-ritalinic acid as an industrial procedure and gives d-threo-ritalinic acid hydrochloride with high optical purity.

More particularly, the process involves the resolution of di-threo-ritalinic acid with (+)-dibenzoyl-D-tartaric acid to yield the desired tartrate salt of d-threo-isomer of ritalinic acid in the first step and the breaking of salt in the second step to obtain the hydrochloride form of the d-threo-isomer with high optical purity, while the l-threo-isomer and the dibenzoyltartaric acid are recovered from the mother liquors as shown below:

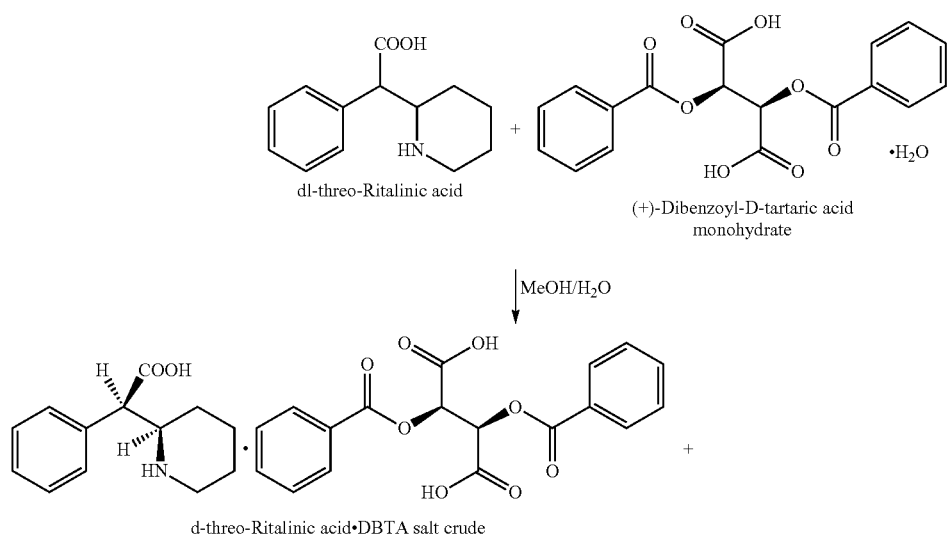
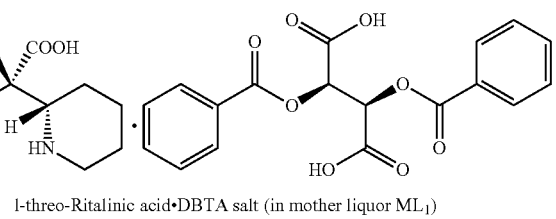
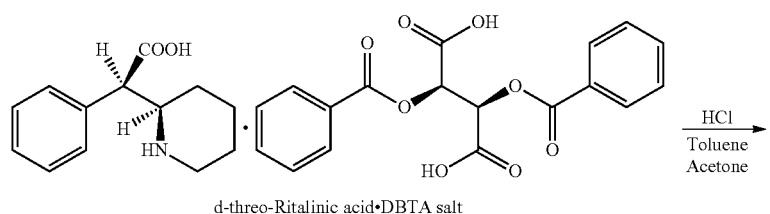
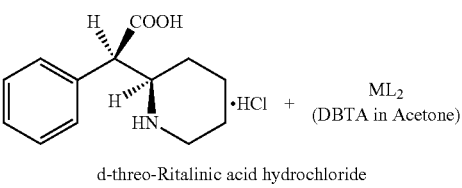
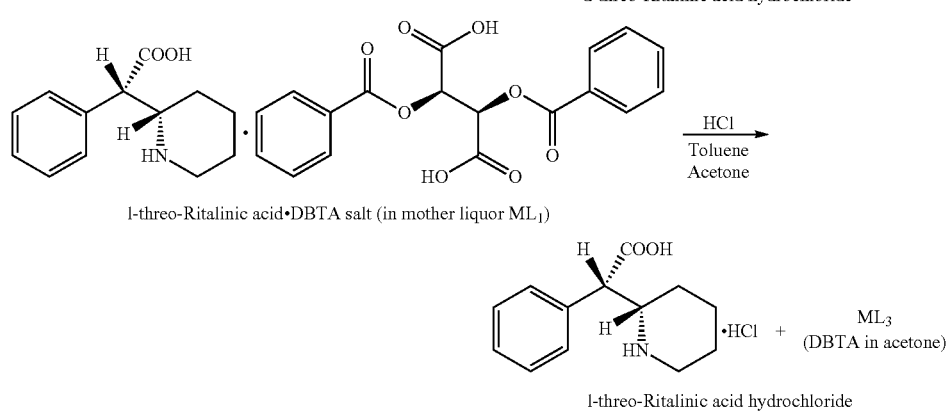

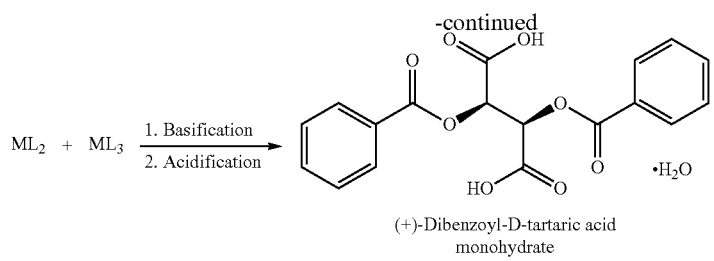

(+)-Dibenzoyl-D-tartaric acid monohydrate

OBJECTIVES OF THE INVENTION

The main objective of the present invention is to provide an improved process for the resolution of dl-threo-ritalinic acid Another objective of the present invention is to provide an improved process for the preparation of d-threo-ritalinic acid hydrochloride and l-threo-ritalinic acid hydrochloride by resolving the dl-threo-ritalinic acid using chiral carboxylic acid as the resolving agent.

Another objective of the present invention is to provide an improved process for the preparation of d-threo-ritalinic acid hydrochloride by resolving the dl-threo-ritalinic acid involving the use of stoichiometric quantity of the resolving agent.

Still another objective of the present invention is to provide an improved process for the preparation of d-threo-ritalinic acid hydrochloride by resolving the dl-threo-ritalinic acid with reduced process steps for isolating d-threo-ritalinic acid in high optical purity of >99%.

Yet another objective of the present invention is to provide an improved process for the preparation of d-threo-ritalinic acid hydrochloride by resolving the dl-threo-ritalinic acid involving the recovery of derivative of tartaric acid from the mother liquors with highest yield.

As a result, the present invention provides a simple but efficient, economical, less time consuming and less tedious method for producing d-threo-ritalinic acid hydrochloride.

DETAILED DESCRIPTION OF THE INVENTION

Accordingly, the present invention provides an improved process for the preparation of d-threo-ritalinic acid hydrochloride and l-threo-ritalinic acid hydrochloride by resolution of dl-threo-ritalinic acid using chiral carboxylic acid which comprises of (i) dissolving dl-threo-ritalinic acid in a solvent, water mixture (60:40) and adding a solution of an ester of tartaric acid in a solvent to the dissolved dl-threo-ritalinic acid solution at a temperature in the range from −10° C. to 100° C. for a period ranging from 5 min to 5 h.

(ii) heating the mass to reflux for a period ranging from 15 min to 24 h and filtering it through the hyflo bed and cooling the filtrate to a temperature in the range of −10° C. to 40° C. to obtain a slurry containing solid mass of d-threo-ritalinic acid-tartaric acid ester salt.

(iii) maintaining the resulting slurry for a period ranging from 30 min to 24 h and filtering to obtain d-threo-ritalinic acid-tartaric acid ester salt.

(iv) adding to the mother liquor, concentrated or dilute hydrochloric acid, solvent and concentrating the mother liquor under vacuum by maintaining temperature 40° C. to 100° C.

(v) adding organic solvent to the concentrated mother liquor.

(vi) cooling the mass to a temperature in the range of −15° C. to 40° C. and filtering to get l-threo-ritalinic acid hydrochloride and the mother liquor containing the resolving agent.

(vii) adding organic solvent and water along with organic or inorganic acids to the d-threo-ritalinic acid-tartaric acid ester salt obtained in step (iii) and removing the water present in the acid using the known methods.

(viii) adding an organic solvent to the concentrated mass obtained in step (vii) under stirring at a temperature range of −10° C. to 25° C. and filtering, to get the d-threo-ritalinic acid hydrochloride and the mother liquor containing the resolving agent.

(ix) concentrating the mother liquors obtained in step (vi) and (viii) basifying and acidifying by conventional methods and filtering the resolving agent.

The dl-threo-ritalinic acid used in step (i) may be prepared through multi-step process in which 2-chloropyridine and benzyl cyanide initially are coupled to form α-pyrid-2-yl-phenylacetonitrile. The resulting α-pyridyl-2-ylphenylacetonitrile then is hydrated in the presence of acid to yield α-pyrid-2-ylphenylacetamide which in turn is catalytically hydrogenated to yield α-piperid-2-ylphenylacetamide and then is hydrolysed and epimerized to dl-threo-ritalinic acid. The solvent used in the step (i) along with water may be selected from organic solvents. The solvent used to dissolve ester of tartaric acid may be selected from organic solvents. Conventional esters of tartaric acid used, may include dibenzoyltartaric acid and ditoluoyltartaric acid, the preferred one being (+)-dibenzoyltartaric acid of 0.2 to 1.6 eq to that of ritalinic acid, preferably, 1.06 eq in a solvent, preferably methanol adding at a temperature ranging preferably below 50° C., for a period preferably ranging from 5 min to 5 h. Heating the mass in step (ii) at reflux temperature preferably in 1 h to 2 h and filtering the mass through hyflo bed. The filtrate is cooled to a temperature preferably 20° C. to 25° C.

The resulting mass of step (iii) is maintained under stirring preferably for 13 h before filtering the d-threo-ritalinic acid-tartaric acid ester salt.

The mother liquor of step (iii) is concentrated under vacuum at a temperature preferably 70° C. to 80° C. after the addition of concentrated or dilute hydrochloric acid along with solvent preferably toluene. The solvent used in step (v) may be selected from water, aliphatic ketones or alcohols, the preferred one being acetone.

The mass obtained is cooled in step (vi) to a temperature in the range −15° C. to 40° C., preferably 10° C. before filtering the l-threo-ritalinic acid hydrochloride.

In step (vii), the solvents like aliphatic ketones or aromatic ketones or alcohols or aromatic/aliphatic hydrocarbons preferably toluene are added to d-threo-ritalinic acid-tartaric acid ester salt along with organic or inorganic acids, preferably hydrochloric acid and heated to evaporate the solvent.

In step (viii), solvents like aliphatic ketones or aromatic ketone or alcohols preferably acetone is added under stirring for preferably 15 min to 30 min at a temperature range of −10° C. to 25° C. preferably 5° C. to 10° C. while filtering the d-threo-ritalinic acid salt. The mother liquors of steps (vi) and (viii) are concentrated together, diluted with water and basified. The ester of tartaric acid formed was filtered after acidification.

The details of the invention are given in the examples given below which are provided solely to illustrate the invention and therefore should not be construed to limit the scope of the invention.

Example 1

| di-threo-Ritalinic acid | 100 g |
| (+)-Dibenzoyl-D-tartaric acid | 182 g |
| Methanol | 2.3 L |
| Water | 1.8 L |
| Acetone | 175 mL |
| HCl | 65 mL |
| Toluene | 450 mL | di-threo-Ritalinic acid (100 g, 0.456 mole) was dissolved in methanol-water mixture (1.8 L and 1.6 L) at room temperature and stirred for 15 min.

(+)-Dibenzoyl-D-tartaric acid (182 g, 0.483 moles) was dissolved in 300 mL of methanol and was added at a temperature below 50° C. in 30 min. The resulting mass was heated to reflux temperature 78° C. to 85° C. and maintained for 1 h to 2 h. The mass was filtered through hyflo bed and washed with 200 mL of water-methanol mixture (1:1). The filtrate was cooled to 20° C. to 25° C. and maintained for 13 h. The precipitated material out was filtered and washed with 200 mL of chilled water-methanol mixture (1:1) to obtain 132 g d-threo-ritalinic acid-dibenzoyl tartaric acid salt.

The mother liquor obtained was treated with 35 mL of conc. hydrochloric acid, 225 mL of toluene and concentrated under vacuum by maintaining a temperature of 70° C. to 80° C. On addition of 100 mL of acetone to the residue and on cooling to 10° C. followed by filtration 45 g of 1-threo-ritalinic acid hydrochloride was isolated.

| Purity by HPLC | 99.78% |
| Chiral purity | 99.05% |
| Yield | 90% |
| mp | 236° C.-240° C. |
| $[\alpha]_D$ | −88.5° (c = 2% in methanol) |

To 132 g of d-threo-ritalinic acid-dibenzoyl tartaric acid salt, toluene 225 mL, 100 mL water and 30 mL of 35% hydrochloric acid were added and concentrated under vacuum by maintaining temperature of 60° C. to 65° C. On addition of 75 mL of acetone to the residue and on cooling to 5° C. to 10° C. followed by filtration, 46 g of d-threo-ritalinic acid hydrochloride was obtained.

| Purity by HPLC | 99.92% |
| Chiral purity | 99.95% |
| Yield | 92% |
| mp | 238° C.-240° C. |
| $[\alpha]_D$ | +89.08° (c = 2% in methanol) |

Respective mother liquors obtained from the d-threo-ritalinic acid hydrochloride and the l-threo-ritalinic acid hydrochloride were concentrated, basified and acidified to recover (+)-dibenzoyl-D-tartaric acid in 90% yield showing optical rotation of −113° and melting point 88° C.-93° C.

Spectroscopic Interpretation

The structure of the product, d-threo-ritalinic acid hydrochloride was confirmed with the help of the following spectroscopic data.

a) IR (cm$^{-1}$) (KBr)

O—H str. of bonded COOH group at 3150-2710, H$\overset{+}{N}$-H str. at 2567, 2509, C=O str. of COOH group at 1709, benzenoid bands at 1585, 1456, C—N str. at 1396, C—O str. at 1182, C—H out of plane bending of mono-substituted benzene ring at 729,704.

b) $^1$H NMR (DMSO-d$_6$, 300 MHz) ($\delta_H$)

1.24-1.66 (6H, m, —NH—CH$_2$—CH$_2$—CH$_2$ of piperidyl ring), 2.96 (1H, s, Ha of

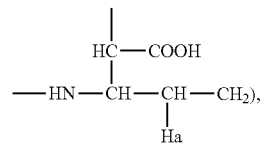

3.29 (1H, d, Hb of

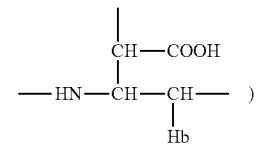

[where Ha and Hb are diastereotopic protons], 3.73 (1H, s, —CH—CH—NH—), 4.08 (1H, d, Ph-CH—COOH), 7.27-7.43 (5H, m, aromatic protons), 8.67 (1H, bs, NH proton), 9.73 (1H, bs, COOH proton).

c) $^{13}$C NMR (DMSO-d$_6$, 300 MHz) ($\delta_c$)

21.29 (—NH—CH$_2$—CH$_2$—CH$_2$), 21.44 (—NH—CH—CH$_2$), 25.50 (—NH—CH$_2$—CH$_2$), 44.56 (—NH—CH$_2$—), 53.21 (Ph-CH—CH—NH), 56.69 (Ph-CH—COOH), 127.85-134.89 (aromatic protons), 172.38 (CH—COOH).

d) Mass Spectrum (EI)

[M]$^{+\cdot}$ at m/z 220 (<1), [M$^+$-CO$_2$] at m/z 175 (2), [M$^+$-C$_5$H$_9$N] at m/z 136 (2),

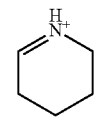

at m/z 84 (100), tropylium cation at m/z 91 (11), [m/z 84-(CH$_2$N)] at m/z 56 (21).

ADVANTAGES OF THE INVENTION

1. The process uses resolving agent which is easily available
2. The resolving agent used can be recovered almost quantitatively.
3. Resolution process is simple as it requires lesser number of steps and the d-threo-ritalinic acid is obtained in >99% optical purity in >90% of theoretical yield (first crop).
4. The process is very economical and useful for commercial production as the variable cost is very low.

We claim:

1. A process for preparation of d-threo-Ritalinic acid & l-threo-Ritalinic acid of formulas I & II and their salts

d-threo-Ritalinic acid (Formula I)

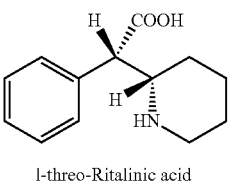

l-threo-Ritalinic acid (Formula II)

by resolution of dl-threo-ritalinic acid of formula III using ester of tartaric acid of formula IV which comprises

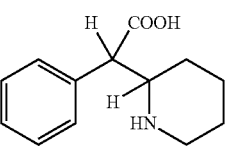

dl-threo-Ritalinic acid (Formula III)

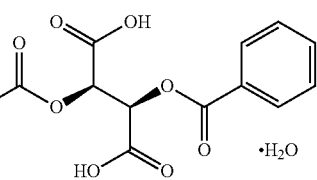

(+)-Dibenzoyl-D-tartaric acid monohydrate (Formula IV)

(i) dissolving dl-threo-ritalinic acid in a solvent, water mixture (60:40) and adding a solution of an ester of tartaric acid dissolved in a first organic solvent to the solution at a temperature in the range from −10° C. to 100° C. for a period ranging from 5 minutes to 5 hours to obtain a resulting mass;
(ii) heating the resulting mass to reflux for a period ranging from 15 minutes to 24 hours and filtering through a hyflo bed, cooling filtrate to a temperature in the range of −10° C. to 40° C. to obtain a slurry containing solid mass of d-threo-ritalinic acid-tartaric acid ester salt;
(iii) maintaining the slurry for a period ranging from 30 minutes to 24 hours and filtering to obtain a first mother liquor, separating d-threo-ritalinic acid-tartaric acid ester salt;
(iv) adding to the first mother liquor, concentrated or dilute hydrochloric acid along with toluene and concentrating under vacuum by maintaining the temperature at 40° C. to 100° C. to obtain an organic residue;
(v) adding a second organic solvent to the organic residue;
(vi) cooling the second organic solvent added to the organic residue to a temperature in the range of −15° C. to 40° C. and filtering to get l-threo-ritalinic acid hydrochloride and the second mother liquor containing a resolving agent;
(vii) adding a third organic solvent along with organic or inorganic acids to the d-threo-ritalinic acid-tartaric acid ester salt and removing water present in the acids to obtain a concentrated mass;
(viii) adding a fourth organic solvent to the concentrated mass at a temperature range of −10° C. to 25° C. and filtering the d-threo-ritalinic acid hydrochloride and separating a third mother liquor containing the resolving agent; and
(ix) concentrating the second and third mother liquors, basifying and acidifying and filtering the resolving agent.

2. The process as claimed in claim 1 wherein the dl-threo-ritalinic acid used is dissolved in a methanol and water mixture, the ester of tartaric acid (Formula IV) used is selected from dibenzoyltartaric acid and ditoluoyltartaric acid, the ester of tartaric acid used is 0.2 to 1.6 eq to that of the base used, the first organic solvent used is methanol and is carried at a temperature in the range of −10° C. to 100° C. for a period ranging from 5 minutes to 5 hours.

3. The process as claimed in claim 2 wherein the resulting mass is heated to a reflux temperature of the methanol and water mixture for a period ranging from 15 minutes to 24 hours and filtering through the hyflo bed, and the filtrate is cooled to a temperature in the range of 20° C. to 25° C.

4. The process as claimed in claim 3 wherein the slurry is maintained for 13 hours to obtain the first mother liquor, separating d-threo-ritalinic acid-tartaric acid ester salt.

5. The process as claimed in claim 4, wherein concentrated hydrochloric acid is added along with toluene to the first mother liquor and the first mother liquor is concentrated under vacuum at a temperature of 70° C. to 80° C.

6. The process as claimed in claim 5 wherein the second organic solvent is acetone.

7. The process as claimed in claim 6 wherein cooling the organic residue containing the second organic solvent is effected at 10° C.

8. The process as claimed in claim 7 wherein the third organic solvent is toluene and the organic or inorganic acid is hydrochloric acid.

9. The process as claimed in claim 8 wherein the fourth organic solvent is selected from water, aliphatic ketones or alcohols.

10. The process as claimed in claim 9 wherein the second and third mother liquors are concentrated together, diluted with water and basified, wherein the ester of tartaric acid formed is filtered after acidification.

11. The process as claimed in claim 1 wherein the resulting mass is heated to a reflux temperature of the methanol and water mixture for a period ranging from 15 minutes to 24 hours and filtering through the hyflo bed, and the filtrate is cooled to a temperature in the range of 20° C. to 25° C.

12. The process as claimed in claim 1 wherein the slurry is maintained for 13 hours to obtain the first mother liquor, separating d-threo-ritalinic acid-tartaric acid ester salt.

13. The process as claimed in claim 1, wherein concentrated hydrochloric acid is added along with toluene to the first mother liquor and the first mother liquor is concentrated under vacuum at a temperature of 70° C. to 80° C.

14. The process as claimed in claim 1 wherein the second organic solvent is acetone.

15. The process as claimed in claim 1 wherein cooling the organic residue containing the second organic solvent is effected at 10° C.

16. The process as claimed in claim 1 wherein the third organic solvent is toluene and the organic or inorganic acid is hydrochloric acid.

17. The process as claimed in claim 1 wherein the fourth organic solvent is selected from water, aliphatic ketones or alcohols.

18. The process as claimed in claim 1 wherein the second and third mother liquors are concentrated together, diluted with water and basified, wherein the ester of tartaric acid formed is filtered after acidification.

* * * * *